United States Patent
Dongara et al.

(10) Patent No.: US 10,781,382 B2
(45) Date of Patent: Sep. 22, 2020

(54) METHODS FOR PRODUCING AROMATICS AND OLEFINS

(71) Applicant: SABIC Global Technologies B.V., Bergen op Zoom (NL)

(72) Inventors: Rajeshwer Dongara, Bangalore (IN); Pankaj Mathure, Bangalore (IN); Mohammad Basheer Ahmed, Bangalore (IN); Venugopal Bv, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/774,206

(22) PCT Filed: Nov. 7, 2016

(86) PCT No.: PCT/IB2016/056683
§ 371 (c)(1),
(2) Date: May 7, 2018

(87) PCT Pub. No.: WO2017/081595
PCT Pub. Date: May 18, 2017

(65) Prior Publication Data
US 2018/0327676 A1 Nov. 15, 2018

Related U.S. Application Data

(60) Provisional application No. 62/254,444, filed on Nov. 12, 2015.

(51) Int. Cl.
*C10G 69/02* (2006.01)
*C07C 4/02* (2006.01)
(Continued)

(52) U.S. Cl.
CPC ............ *C10G 69/02* (2013.01); *B01J 8/1863* (2013.01); *B01J 8/28* (2013.01); *C07C 4/14* (2013.01);
(Continued)

(58) Field of Classification Search
CPC .... C07C 4/14; C07C 4/02; C07C 4/08; C07C 4/12; C07C 4/00; C10G 69/02
See application file for complete search history.

(56) References Cited

U.S. PATENT DOCUMENTS 3,291,850 A * 12/1966 Carson ...................... C07C 4/18
585/483
3,556,987 A 1/1971 Zimmerman et al. .......... 208/93
(Continued)

FOREIGN PATENT DOCUMENTS

| CA | 2219137 | 10/1996 |
|---|---|---|
| CA | 2210930 | 1/1999 |

(Continued)

OTHER PUBLICATIONS

"Naphtha Hydrotreating Process." Axens IFP Group Technologies. http://www.axens.net/product/technology-licensing/10025/naphtha-hydrotreating-process.html.
(Continued)

*Primary Examiner* — Youngsul Jeong
(74) *Attorney, Agent, or Firm* — Norton Rose Fulbright US LLP (57) ABSTRACT

The presently disclosed subject matter provides methods for producing olefins and/or aromatics from coker naphtha. In a non-limiting embodiment, a method for producing aromatics includes hydrogenating the coker naphtha stream in the presence of a first catalyst to remove diolefins and sulfur, if any, to obtain a hydrogenated stream and subjecting the hydrogenated stream to aromatization in the presence of a (Continued)

second catalyst to produce an aromatic-rich stream that includes benzene, toluene and xylene. In certain embodiments, a method for producing olefins includes hydrogenating the coker naphtha stream in the presence of a first catalyst to remove diolefins and sulfur, if any, to obtain a hydrogenated stream and subjecting the hydrogenated stream to catalytic cracking in the presence of a second catalyst to produce an olefin-rich stream that includes ethylene, propylene and aromatics.

16 Claims, 3 Drawing Sheets

(51) Int. Cl.

| | | |
|---|---|---|
| C07C 4/06 | (2006.01) | |
| C10G 63/04 | (2006.01) | |
| C10G 65/12 | (2006.01) | |
| C10G 11/18 | (2006.01) | |
| C10G 21/00 | (2006.01) | |
| C10G 47/30 | (2006.01) | |
| C10G 45/40 | (2006.01) | |
| C10G 45/02 | (2006.01) | |
| C10G 25/00 | (2006.01) | |
| C10G 9/30 | (2006.01) | |
| C10G 65/04 | (2006.01) | |
| C10G 45/38 | (2006.01) | |
| C10G 45/70 | (2006.01) | |
| C10G 11/05 | (2006.01) | |
| B01J 8/28 | (2006.01) | |
| B01J 8/18 | (2006.01) | |
| C10G 35/085 | (2006.01) | |
| C10G 35/14 | (2006.01) | |
| C07C 4/14 | (2006.01) | |

(52) U.S. Cl.
CPC ............... *C10G 9/30* (2013.01); *C10G 11/05* (2013.01); *C10G 11/18* (2013.01); *C10G 21/00* (2013.01); *C10G 25/003* (2013.01); *C10G 35/085* (2013.01); *C10G 35/14* (2013.01); *C10G 45/02* (2013.01); *C10G 45/38* (2013.01); *C10G 45/40* (2013.01); *C10G 45/70* (2013.01); *C10G 47/30* (2013.01); *C10G 63/04* (2013.01); *C10G 65/046* (2013.01); *C10G 65/12* (2013.01); *C07C 2523/26* (2013.01); *C07C 2529/44* (2013.01); *C07C 2529/48* (2013.01); *C10G 2400/30* (2013.01)

(56) References Cited

U.S. PATENT DOCUMENTS

| | | | | |
|---|---|---|---|---|
| 3,647,682 | A | 3/1972 | Rabo et al. ............... 208/120.15 |
| 3,758,403 | A | 9/1973 | Rosinski et al. .................. 502/67 |
| 3,785,782 | A | 1/1974 | Cartmell ....................... 422/144 |
| 4,053,388 | A | 10/1977 | Bailey ............................ 208/89 |
| 4,138,325 | A | 2/1979 | Beuther et al. .................. 208/50 |
| 4,176,047 | A | 11/1979 | Orrell et al. ..................... 208/67 |
| 4,179,474 | A | 12/1979 | Beuther et al. ................. 585/251 |
| 4,404,095 | A | 9/1983 | Haddad et al. ................. 208/161 |
| 4,419,221 | A | 12/1983 | Castagnos, Jr. et al. ...... 208/113 |
| 4,436,945 | A * | 3/1984 | Koya ..................... B01J 29/48 585/486 |
| 4,645,587 | A * | 2/1987 | Kokayeff ............. C10G 25/003 208/296 |
| 4,814,067 | A | 3/1989 | Gartside et al. ............... 208/127 |
| 4,828,679 | A | 5/1989 | Cormier et al. .......... 208/120.05 |
| 5,552,033 | A | 9/1996 | Shih .............................. 208/89 |
| 5,685,972 | A | 11/1997 | Timken et al. .................. 208/89 |
| 5,865,987 | A | 2/1999 | Borghard et al. ................ 208/97 |
| 5,932,777 | A * | 8/1999 | Sughrue, II ............ C10G 61/00 585/322 |
| 6,153,089 | A | 11/2000 | Das et al. ....................... 208/134 |
| 6,740,788 | B1 | 5/2004 | Maher et al. .................. 585/319 |
| 8,685,232 | B2 * | 4/2014 | Mandal .................. C10G 11/18 208/118 |
| 8,778,170 | B2 | 7/2014 | Long et al. ...................... 208/75 |
| 8,940,950 | B2 | 1/2015 | Ellrich et al. .................. 585/319 |
| 8,962,900 | B2 | 2/2015 | Kim et al. ..................... 585/251 |
| 8,975,462 | B2 | 3/2015 | Kim et al. ..................... 585/323 |
| 2005/0014639 | A1 | 1/2005 | Bhan et al. ..................... 502/313 |
| 2005/0197515 | A1* | 9/2005 | Juttu ........................ B01J 29/87 585/418 |
| 2008/0156696 | A1 | 7/2008 | Niccum et al. .................. 208/78 |
| 2012/0273394 | A1 | 11/2012 | Banerjee et al. ............. 208/264 |
| 2013/0056393 | A1 | 3/2013 | Subramani et al. ............ 208/74 |
| 2013/0118953 | A1 | 5/2013 | Zhang et al. .................... 208/92 |
| 2014/0275671 | A1 | 9/2014 | Kim et al. ..................... 585/251 |

FOREIGN PATENT DOCUMENTS

| | | | |
|---|---|---|---|
| CA | 2309093 | C | 5/2009 |
| CN | 102382678 | | 2/2014 |
| CN | 102795958 | | 3/2015 |
| CN | 103374395 | | 7/2015 |
| CN | 104031679 | | 5/2016 |
| EP | 0819157 | | 1/2002 |
| EP | 1188811 | | 7/2004 |
| EP | 1063013 | | 10/2005 |
| GB | 1155416 | * | 6/1969 ............ C07C 15/12 |
| GB | 1155416 | A | 6/1969 |
| KR | 101173345 | | 8/2012 |
| WO | WO 2006/088539 | | 8/2006 |

OTHER PUBLICATIONS

"Naphtha Hydrotreating." Honeywell UOP. http://www.uop.com/processing-solutions/refining/gasoline/naphtha-hydrotreating/.
"Process." Chevron Phillips Chemical Company LLC. http://www.cpchem.com/en-us/rnt/licensing/aromaxtech/Pages/Process.aspx
International Search Report and Written Opinion from PCT/IB2016/056683, dated Feb. 8, 2007, 12 pages.
Robinson et al. "Hydrotreating and Hydrocracking: Fundamentals." Practical Advances in Petroleum Processing, Chapter 7, 2006, 177-218.
"Naptha Hydrotreating Catalysts." Criterion Catalysts & Technologies. Retrieved from https://www.criterioncatalysts.com/products/product-applications/naphtha/_jcr_content/par/expandablelist/expandablesection_854912164.stream/1481725671549/bd958c63a 0e8f2f7baa6eb545ff86622981284871dd0cc924704af911ebc35f/naphtha-hydrotreatingfactsheethires.pdf on Aug. 13, 2018.
Aromatics Complexes: Handbook of Petroleum Refining Processes, Ed: Meyers, R.A., 3rd Edition, Oct. 1, 2004, pp. 2.3-2.10.
Breivik et al. "Coker naphtha hydrotreating. Highly exothermic olefins saturation and silica contamination can occur when hydrotreating coker naphtha." http://www.digitalrefining.com/article/1000153. PTQ Q1 2008. 7 pages.
Encyclopedia of Hydrocarbons (Refining and Petrochemicals) vol. 2, Chapter 10, Fondata da Giovanni Treccani (2005), pp. 407-613.
Lengyel et al. "Upgrading of delayed coker light naphtha in a crude oil refinery." Petroleum & Coal 51(2), pp. 80-90, 2009.
Liu et al. "Recent Advances in Heavy Oil Hydroprocessing Technologies." *Recent Patents on Chemical Engineering*, 2 (2009), pp. 22-36, 2009.
Sanghavi et al. "Achieve success in gasoline hydrotreating." Hydrocarbon Processing, Sep. 2011, pp. 59-61.
Speight, J. "Petroleum Refinery Process." *Kirk-Othmer Encyclopedia of Chemical Technology*. John Wiley & Sons, Inc. 2005. 49 pages.
Tagliabue et al. "Increasing value from steam cracker olefin streams." EniTecnologie SpA, Petrochemicals and Gas Processing, PTQ, Winter 2004, pp. 145-149.

(56) References Cited

OTHER PUBLICATIONS

Wikipedia http://en.wikipedia.org/wiki/HPC_catalysts, Retrieved Aug. 31, 2018.
Yui, Sok. "Removing diolefins from coker naphtha necessary before hydrotreating." Oil & Gas Journal. vol. 97, Issue 36 (1999) p. 64-67. Partial Reference.
Boepple et al. "Catalytic Processing of Crude Residue." Nexant ChemSystems Perp Program. PERP 09/10S6, Report Abstract, Dec. 2011, 7 pages.
Wan, Victor. "Propylene Production." SRI Consulting, PEP Report 267, Oct. 2008, Abstract only, 13 pages.

* cited by examiner

METHODS FOR PRODUCING AROMATICS AND OLEFINS

CROSS-REFERENCE TO RELATED APPLICATIONS

This application is a national phase application under 35 U.S.C. § 371 of International Application No. PCT/IB2016/056683 filed Nov. 7, 2016, which claims priority to U.S. Provisional Patent Application No. 62/254,444 filed Nov. 12, 2015. The entire contents of each of the above-referenced disclosures is specifically incorporated by reference herein without disclaimer.

FIELD

The presently disclosed subject matter relates to methods for producing aromatics and olefins from coker naphtha.

BACKGROUND

A coker is an oil refinery processing unit that can convert the residual oil from a vacuum distillation column or an atmospheric distillation column into low molecular weight hydrocarbon gases, naphtha, e.g., coker naphtha, light and heavy gas oils and petroleum coke. The coker process can thermally crack the long chain hydrocarbon molecules in the residual oil feed into shorter chain molecules leaving behind the excess carbon in the form of petroleum coke. Coker naphtha, a low value refinery stream of the coker, can contain large amount of unsaturated hydrocarbons like olefins, diolefins and aromatics, as well as sulfur, silica and nitrogen. Such aromatics, e.g., benzene, toluene and xylene, are petrochemical raw materials that can be used for polymer and other petrochemical syntheses, and are in demand. The generation of high quality hydrocarbon products from coker naphtha, e.g., aromatic-rich streams, can be difficult due to the presence of diolefins, sulfur and silica within the coker naphtha that can lead to reactor fouling.

Certain methods for generating olefins and aromatics are known in the art. U.S. Pat. No. 8,975,462 discloses a method for manufacturing high value aromatics and olefinic products from light cycle oils or oil fractions containing aromatic compounds, which can include hydroprocessing an oil fraction in the presence of a catalyst to partially saturate aromatic components, followed by catalytic cracking partially saturated components in the presence of a catalyst to produce monoaromatics. U.S. Pat. No. 5,685,972 discloses a method for producing benzene, toluene and xylene from a naphtha feed with sulfur impurities while co-producing a low sulfur gasoline with a relatively high octane number. U.S. Pat. No. 5,552,033 discloses an integrated process for increasing $C_6$ to $C_8$ aromatics content in a reformate prepared from $C_{9+}$ aromatics-containing naphtha. U.S. Patent Publication No. 2014/0275671 discloses a method for producing aromatic hydrocarbons and olefins from hydrocarbonaceous oils through partial hydrogenation in the presence of a hydrogenation catalyst and catalytic cracking in the presence of a catalytic cracking catalyst.

K.R. Patent No. 101173345 discloses a method for producing aromatics and olefins by hydrotreating a hydrocarbonaceous oil in the presence of a catalyst, followed by catalytic cracking the hydrotreated oil to generate a product stream. U.S. Patent Publication No. 2013/0056393 discloses techniques for simultaneous conversion of lighter and heavier hydrocarbon feedstocks into light olefins in the $C_2$-$C_4$ range and liquid aromatic compounds in the $C_6$-$C_8$ range (e.g., benzene, toluene, xylene and ethylbenzene) by employing at least two different reactors operated in series with respect to catalyst flow and parallel with respect to feed flow. C.N. Application No. 104031679 discloses a method for the production of olefins and aromatic hydrocarbons from naphtha.

There is a need for methods for generating olefins and aromatics from a hydrocarbon stream such as coker naphtha.

SUMMARY OF THE DISCLOSED SUBJECT MATTER

The presently disclosed subject matter provides methods for producing aromatics and/or olefins from a hydrocarbon stream such as coker naphtha.

In certain embodiments, a method for producing aromatics from a coker naphtha stream can include hydrogenating the coker naphtha stream in the presence of a first catalyst to remove diolefins and sulfur, if any, to obtain a hydrogenated stream. The method can further include subjecting the hydrogenated stream to aromatization in the presence of a second catalyst to produce an aromatic-rich stream that includes benzene, toluene, and xylene. In certain embodiments, the method can further include removing silica and particulates, if any, from the coker naphtha stream prior to hydrogenation. The second catalyst can have a metal oxide loading about 0.2 to about 1.5 weight % and can be a catalyst such as Ga/Nd/ZSM-5, Ga/Pt/Ge/ZSM-5, Pt/Ga/ZSM-5, Pt/Ge/ZSM-5 or Ni—W/Ga/ZSM-5.

In certain embodiments, the aromatic-rich stream includes at least about 40% of aromatic compounds. The method can further include hydrodealkylating the aromatic-rich stream in the presence of a third catalyst and hydrogen to produce a benzene-rich stream. Alternatively or additionally, the method can include mild hydrocracking of the aromatic-rich stream in the presence of a third catalyst and hydrogen to produce a benzene-rich stream. In certain embodiments, the method can further include extracting benzene from the benzene-rich stream to obtain a purified product stream that includes greater than or equal to about 99% benzene. In certain embodiments, the third catalyst includes chromia-alumina and platinum loaded onto Zeolite-Y.

The presently disclosed subject matter also provides methods for producing aromatics from a coker naphtha stream by removing silica and/or particulates from the coker naphtha stream to obtain a pretreated coker naphtha stream. The method can further include hydrogenating the pretreated coker naphtha stream in the presence of a first catalyst to remove diolefins and sulfur to obtain a hydrogenated stream that includes olefins and aromatics. In certain embodiments, the method can further include subjecting the hydrogenated stream to an aromatization process in the presence of a second catalyst having a metal oxide loading of about 0.2 to about 1.5 weight % and can be a catalyst such as Ga/Nd/ZSM-5, Ga/Pt/Ge/ZSM-5, Pt/Ga/ZSM-5, Pt/Ge/ZSM-5, or Ni—W/Ga/ZSM-5 to produce an aromatic-rich stream that includes at least about 40% of aromatic compounds.

In certain embodiments, the method can include subjecting the hydrogenated stream to an aromatization process in the presence of a catalyst to produce an aromatic-rich stream that includes at least about 40% of aromatic compounds and hydrodealkylating the aromatic-rich stream in the presence of a third catalyst to produce a benzene-rich stream. The method can further include extracting benzene, e.g., by extractive distillation, from the benzene-rich stream to obtain a purified product stream that includes greater than or equal to about 99% benzene.

The presently disclosed subject matter further provides methods for producing olefins from a coker naphtha stream. In certain embodiments, the method includes hydrogenating the coker naphtha stream in the presence of a first catalyst to remove diolefins and sulfur, if any, to obtain a hydrogenated stream. The method can further include subjecting the hydrogenated stream to catalytic cracking in the presence of a second catalyst to produce an olefin-rich stream that includes ethylene, propylene, and aromatics. In certain embodiments, the method can further include removing silica and particulates, if any, from the coker naphtha stream prior to hydrogenation. In certain embodiments, the second catalyst has a metal oxide loading of about 2 to about 10 weight % and is a catalyst such as Ga/Nd/ZSM-5, Ga/Pt/Ge/ZSM-5, Pt/Ga/ZSM-5, Pt/Ge/ZSM-5, or Ni—W/Ga/ZSM-5. In certain embodiments, the olefins-rich stream includes greater than about 55% of olefins.

DETAILED DESCRIPTION

The presently disclosed subject matter provides methods for olefin production and/or aromatic production from a hydrocarbon feedstream. In certain embodiments, the methods of the present disclosure can be used to produce monoaromatics, e.g., benzene and toluene, and/or olefins from coker naphtha using high stability catalysts.

Figure 1:
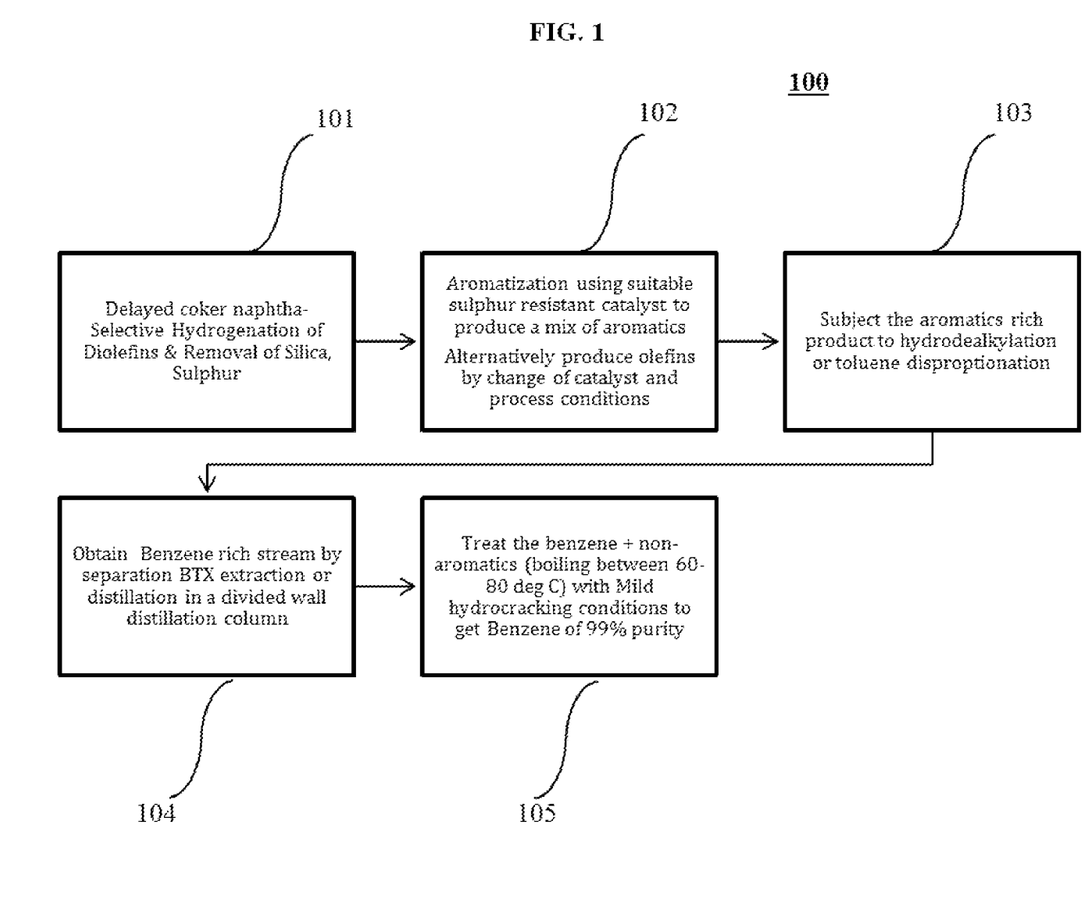
FIG. 1 is a schematic diagram depicting an exemplary method in accordance with one non-limiting embodiment of the disclosed subject matter.
Figure 2:
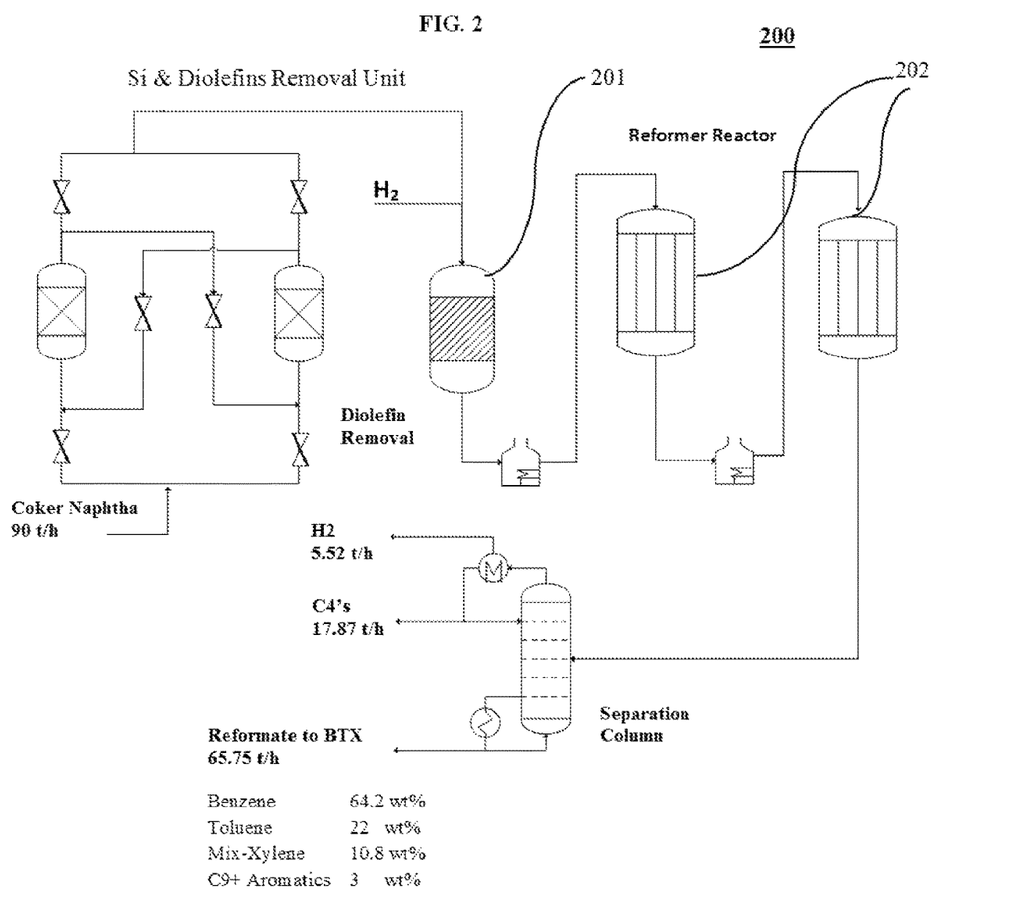
FIG. 2 is a schematic diagram depicting an exemplary method in accordance with one non-limiting embodiment of the disclosed subject matter.
Figure 3:
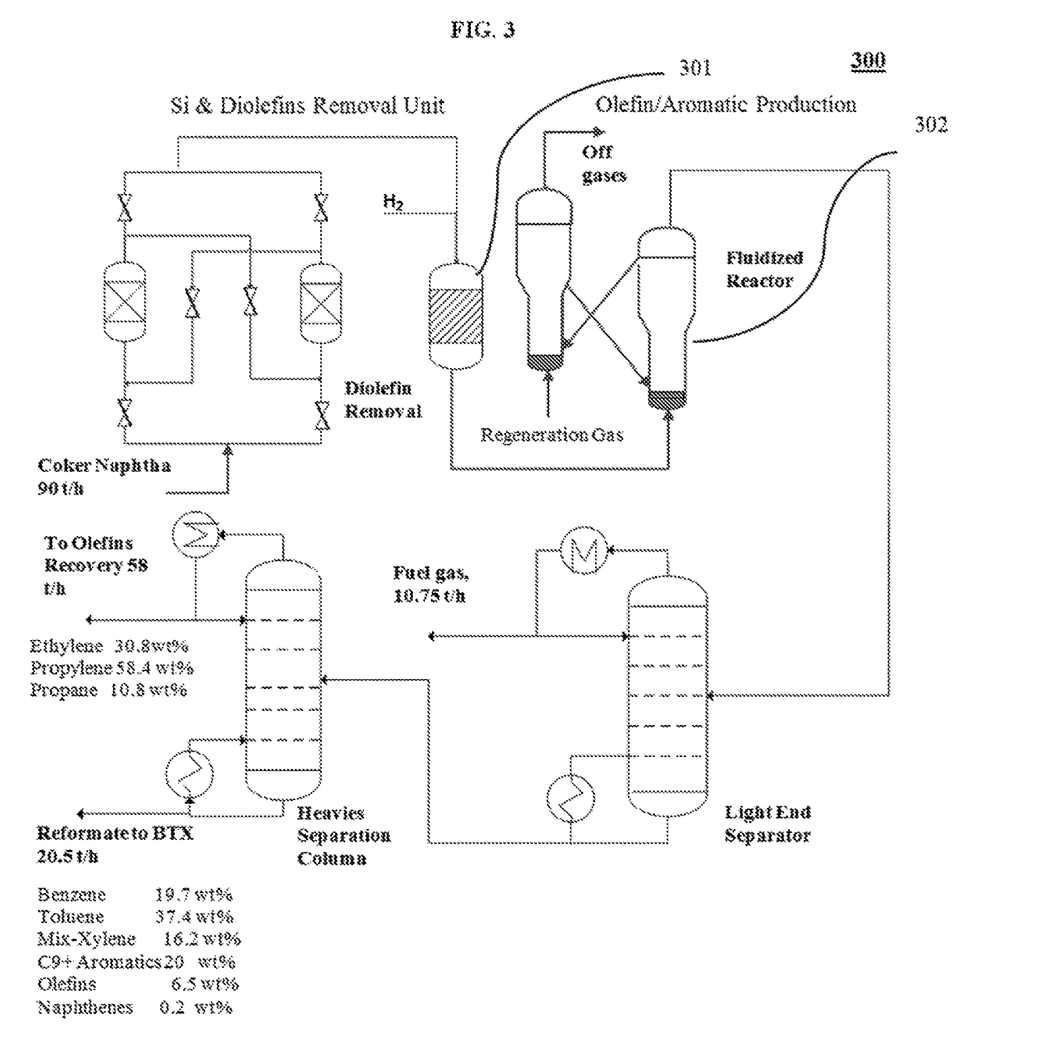
FIG. 3 is a schematic diagram depicting an exemplary method in accordance with one non-limiting embodiment of the disclosed subject matter.

For the purpose of illustration and not limitation, FIGS. 1, 2, and 3 are schematic representations of methods according to non-limiting embodiments of the disclosed subject matter. In certain embodiments, the method 100, 200, or 300 can include providing one or more hydrocarbon feedstreams. Non-limiting examples of such hydrocarbon feedstreams include naphtha streams, e.g., coker naphtha or straight-line naphtha. For example, and not by way of limitation, the hydrocarbon feedstream can be coker naphtha, e.g., obtained from a delayed coker. In certain embodiments, the coker naphtha can have a boiling point from about 25° C. to about 85° C. In certain embodiments, the hydrocarbon feedstream can include from about 20% to about 70% paraffins, from about 20% to about 45% olefins, from about 0.01% to about 3% diolefins, from about 5% to about 15% naphthenes, and/or from about 0.5% to about 5% aromatics. A non-limiting embodiment of the hydrocarbon feedstream that can be used in the presently disclosed subject matter is shown in FIG. 2.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5% and/or up to 1% of a given value.

In certain embodiments, the method 100, 200, or 300 can include hydrogenating the hydrocarbon feedstream in the presence of a first catalyst and hydrogen to remove diolefins to obtain a hydrogenated feedstream 101, 201, or 301. Non-limiting examples of diolefins that can be removed from the hydrocarbon feedstream include butadienes, pentadienes, 2-methyl-1,3-butadiene, 1-trans-3-pentadiene, 1-cis-3-pentadiene, and 2-methyl-1,4-pentadiene. In certain embodiments, the diolefins can be removed by the hydrogenation of such diolefins into olefins. In certain embodiments, the method can further include removing sulfur, if any, from the hydrocarbon feedstream, e.g., sulfur can be removed from the hydrocarbon feedstream by the hydrogenation of the sulfur to hydrogen sulfide. Non-limiting examples of the first catalyst can include a cobalt and/or molybdenum-based catalyst. In certain embodiments, the method can further include removing nitrogen from the hydrocarbon feedstream, e.g., by converting nitrogen into ammonia. In certain embodiments, the hydrogen sulfide and/or ammonia can be removed from the hydrogenated feedstream by stripping. In certain embodiments, hydrogenation of sulfur, diolefins and/or nitrogen can occur simultaneously within the same step or can occur by different processes and at different timepoints within the methods of the disclosed subject matter. For example, and not by way of limitation, the sulfur and/or nitrogen can be removed from the hydrocarbon feedstream followed by the hydrogenation of diolefins within the hydrocarbon feedstream.

In certain embodiments, hydrogenation of the sulfur and/or nitrogen within the hydrocarbon stream can occur at a temperature from about 320 to about 450° C., e.g., from about 350 to about 450° C., from about 375 to about 450° C., from about 400 to about 450° C. or from about 425 to about 450° C. In certain embodiments, the pressure can be from about 50 kg/cm² g to about 60 kg/cm² g. For example, and not by way of limitation, the pressure can be from about 50 kg/cm² g to about 60 kg/cm² g, from about 52 kg/cm² g to about 60 kg/cm² g, from about 54 kg/cm² g to about 60 kg/cm² g, 56 kg/cm² g to about 60 kg/cm² g or from about 58 kg/cm² g to about 60 kg/cm² g. The sulfur and/or nitrogen hydrogenation process can be performed at a hydrogen to hydrocarbon feedstream ratio of about 200 to about 450 Nm³/m³ of hydrogen to hydrocarbon feedstream, e.g., about 220 to about 450 Nm³/m³, about 240 to about 450 Nm³/m³, about 260 to about 450 Nm³/m³, about 280 to about 450 Nm³/m³, about 300 to about 450 Nm³/m³, about 320 to about 450 Nm³/m³, about 340 to about 450 Nm³/m³, about 360 to about 450 Nm³/m³, about 380 to about 450 Nm³/m³, about 300 to about 450 Nm³/m³, about 320 to about 450 Nm³/m³, about 340 to about 450 Nm³/m³, about 360 to about 450 Nm³/m³, about 380 to about 450 Nm³/m³, about 400 to about 450 Nm³/m³ or about 420 to about 450 Nm³/m³ hydrogen to hydrocarbon feedstream. In certain embodiments, the liquid hourly space velocity (LHSV) of the hydrogenation process can be from about 2 to about 12 per hour, e.g., from about 3 to about 12 per hour, from about 4 to about 12 per hour, from about 5 to about 12 per hour, from about 6 to about 12 per hour, from about 7 to about 12 per hour, from about 8 to about 12 per hour, from about 9 to about 12 per hour, from about 10 to about 12 per hour or from about 11 to about 12 per hour.

In certain embodiments, hydrogenation of the diolefins within the hydrocarbon stream can occur at a temperature from about 450 to about 530° C., e.g., from about 460 to about 530° C., from about 470 to about 530° C., from about 480 to about 530° C., 490 to about 530° C., 450 to about 530° C., 500 to about 530° C., 510 to about 530° C. or from about 520 to about 530° C. In certain embodiments, the pressure can be from about 500 to about 740 psi$_a$, e.g., from about 540 to about 740 psi$_a$, from about 580 to about 740 psi$_a$, from about 620 to about 740 psi$_a$, from about 640 to about 740 psi$_a$, from about 680 to about 740 psi$_a$ or from about 720 to about 740 psi$_a$. The diolefin hydrogenation process can be performed at a hydrogen to hydrocarbon feedstream ratio of about 80 to 125 Nm$^3$/m$^3$ of hydrogen to hydrocarbon feedstream, e.g., about 90 to about 125 Nm$^3$/m$^3$, about 100 to about 125 Nm$^3$/m$^3$, about 110 to about 125 Nm$^3$/m$^3$ or 120 to about 125 Nm$^3$/m$^3$ of hydrogen to hydrocarbon feedstream. In certain embodiments, the LHSV of the hydrogenation process can be from about 3 to about 7 per hour, e.g., from about from about 4 to about 7 per hour, from about 5 to about 7 per hour or from about 6 to about 7 per hour. Non-limiting examples of hydrogenation processes for the hydrogenation of diolefins that can be used in the disclosed subject matter is provided in U.S. Patent Publication Nos. 2012/0273394 and 2005/0014639, EP1188811 and WO 2006/088539, which are incorporated by reference herein in their entireties.

In certain embodiments, the hydrogenated stream can include greater than about 10%, greater than about 15%, greater than about 20%, greater than about 25%, greater than about 30%, greater than about 35% or greater than about 40% of olefins. Non-limiting examples of olefins include 1-butene, iso-butene, trans-2-butene, cis-2 butene, 3-methyl-1-butene, 1-pentene, 2-methyl-1-butene, cis-2-pentene, trans-2-pentene, 2-methyl-2-butane, cyclopentene, 4-methyl-1-pentene 1-hexene, cis-3-hexene and trans-3-hexene. In certain embodiments, the hydrogenated stream can include greater than about 30%, greater than about 40%, greater than about 50%, greater than about 60% or greater than about 70% paraffins. Non-limiting examples of paraffins include normal (n)-hexane, iso-hexane, n-butane and n-pentane. In certain embodiments, the hydrogenated stream can include from about 20% to about 70% paraffins, from about 20% to about 45% olefins, about 0% diolefins, from about 5% to about 15% naphthenes and/or from about 0.5% to about 5% aromatics. Non-limiting examples of naphthenes include cyclohexene and methylcyclopentane.

In certain embodiments, prior to hydrogenation of the hydrocarbon feedstream, e.g., before hydrogenation of diolefins, sulfur and/or nitrogen, the hydrocarbon feedstream can be treated to remove particulates and/or silicon-based compounds (e.g., silica from the hydrocarbon stream) (see FIGS. 2 and 3 and 101 of FIG. 1). In certain embodiments, coker naphtha fractions can contain about 5 to about 20 wt ppm of silicon-based compounds (e.g., polydimethyl siloxane), where the presence of up to about 10 wt ppm can also be observed. The presence of such compounds can poison the catalyst in downstream hydrotreaters thereby significantly reducing the hydrogenation activity of the catalyst. The organic silicon-based compounds can also inactivate the desulfurization catalyst. In certain embodiments, alumina, activated alumina, spent alumina-based desulfurizer catalyst or spent alumina-supported cobalt-molybdenum oxide can be used to remove silicon-based compounds from the hydrocarbon feedstream. See, for example, U.S. Pat. Nos. 4,176,047 and 4,645,587.

In certain embodiments, and as shown in FIG. 1 or 2, the method 100 or 200 can further include subjecting the hydrogenated stream to aromatization in the presence of a second catalyst to produce an aromatic-rich stream 102 or 202. In certain embodiments, the aromatic-rich stream can include greater than about 30%, greater than about 40%, greater than about 50%, greater than about 60%, greater than about 70%, greater than about 80%, greater than about 85%, greater than about 90%, greater than about 91%, greater than about 92%, greater than about 93%, greater than about 94%, greater than about 95%, greater than about 96%, greater than about 97%, greater than about 98% or greater than about 99% aromatics. Non-limiting examples of aromatics can include benzene, toluene, mix-xylene, 1-methyl benzene, ethyl benzene, C9+ aromatics or a combination thereof. For example, and not by way of limitation, the aromatic-rich can include from about 50% to about 70% benzene, e.g., about 64%, from about 10% to about 30% toluene, e.g., about 22%, from about 5% to about 15% toluene, e.g., about 11%, or from about 1% to about 10% C9+ aromatics, e.g., about 3% C9+ aromatics.

In certain embodiments, aromatization of the hydrogenated stream to generate an aromatic-rich stream can occur in a reactor, e.g., a fixed bed reactor, at a pressure from about 500 to about 700 kPa. For example, and not by way of limitation, the pressure can be from about 500 kPa to about 550 kPa, from about 550 kPa to about 600 kPa, from about 600 kPa to about 650 kPa or from about 650 kPa to about 700 kPa. In certain embodiments, the aromatization step can occur at a temperature from about 400 to about 525° C., e.g., from about 425 to about 450° C., from about 450 to about 475° C., from about 475 to about 500° C. or from about 500 to about 525° C. In certain embodiments, the weight hourly space velocity (WHSV) can be from about 0.5 to about 2 per hour.

Alternatively, and as shown in FIG. 1 or 3, the method 100 or 300 can include subjecting the hydrogenated stream to a catalytic cracking process in the presence of a second catalyst to produce an olefin-rich stream 102 or 302. In certain embodiments, in addition to producing olefins, the olefin-rich stream can include aromatics (see FIG. 3). In certain embodiments, the olefin-rich stream can include greater than about 55%, greater than about 60%, greater than about 70% of olefins. In certain embodiments, the olefin-rich stream can include from about 55 to about 65% olefins. Non-limiting examples of olefins include ethylene, propylene and n-butenes. For example, and not by way of limitation, the olefin-rich stream can include from about 20% to about 40% of ethylene, e.g., from about 25% to about 35% or about 20%, and/or from about 50% to about 70% propylene, e.g., from about 30% to about 40%. In certain embodiments, the olefin-rich stream can further include paraffins, e.g., propane, at an amount greater than about 5%, greater than about 10%, greater than about 15% or from about 5 to about 10%. In certain embodiments, the olefin-rich stream can include aromatics, e.g., about 15 to about 25% aromatics, and/or include about 7 to about 15% fuel gas. A non-limiting embodiment of an olefin-rich stream that can be produced in the presently disclosed subject matter is shown in FIG. 3.

In certain embodiments, cracking of the hydrogenated stream to generate an olefin-rich stream can occur in a reactor, e.g., a fluidized bed reactor, at a pressure from about 50 to about 300 kPa. For example, and not by way of limitation, the pressure can be from about 100 kPa to about 300 kPa, from about 150 kPa to about 300 kPa, from about 200 kPa to about 300 kPa or from about 250 kPa to about 300 kPa. In certain embodiments, catalytic cracking can occur at a temperature from about 510 to about 710° C., e.g., from about 550 to about 710° C., from about 600 to about 710° C., from about 650 to about 710° C. or from about 700 to about 710° C. Additional non-limiting examples of processes for producing olefin-rich streams are disclosed in U.S. Pat. Nos. 4,814,067, 4,404,095, 3,785,782, 4,419,221, 4,828,679, 3,647,682, and 3,758,403, and U.S. Patent Publication No. 2008/0156696. In certain embodiments, the aromatics can be separated from the olefins in the olefin-rich stream by using water or oil quenching or by the use of distillation columns as described below.

The catalyst compositions for use as the second catalyst in the methods of the presently disclosed subject matter can include a metal and/or metal oxide. Non-limiting examples of suitable metals include chromium (Cr), copper (Cu), manganese (Mn), potassium (K), palladium (Pd), cobalt (Co), cerium (Ce), tungsten (W), platinum (Pt), sodium (Na) and cesium (Cs) or oxides thereof. In certain embodiments, the catalyst can include Pt, Pt oxide, Ni and/or Ni oxide.

In certain embodiments, the second catalyst can further include an inert carrier or support material. The support material can be any traditional support material known and used in the art. Suitable supports can be any support materials, which exhibit good stability at the reaction conditions of the disclosed methods, and are known by one of ordinary skill in the art. In certain embodiments, the support material can include aluminium oxide (alumina), magnesia, silica, titania, zirconia, and mixtures or combinations thereof. In certain embodiments, the support material is alumina. In certain embodiments, the support includes alumina and silica. In certain embodiments, the support is a zeolite, e.g., ZSM, Zeolite-X, Zeolite-Y or a combination thereof. Additional non-limiting examples of zeolites include USY, REY, RE-USY, faujasite, TEA-mordenite, TEA-ZSM-12, MCM-22, MCM-36, MCM-39, MCM-41, MCM-48, PSH03, ZSM-5, TPA05, Breck 6, ZSM-12, ZSM-22, ZSM-23, ZSM-35, ZSM-48 and SSZ-32. For example, and not by way of limitation, the support can be ZSM-5.

In certain non-limiting embodiments, the second catalyst can further include a promoter component such as rare earth metals, magnesium, rhenium, and alkali metals such as lithium, sodium, potassium, rubidium and cesium. Non-limiting examples of suitable promoters can be selected from the group consisting of lanthanides, alkaline earth metals and combinations thereof. For example, and not by way of limitation, the catalyst can contain a promoter component such as rhenium (Re), sulphur (S), molybdenum (Mo), gallium (Ga), tungsten (W), chromium (Cr), germanium (Ge), neodymium (Nd), and/or iridium (Ir). Non-limiting examples of a second catalyst include Ga/Nd/ZSM-5, Ga/Pt/Ge/ZSM-5, Pt/Ga/ZSM-5, Pt/Ge/ZSM-5 and Ni—W/Ga/ZSM-5.

In certain embodiments, where the method includes aromatization of the hydrogenated stream in the presence of a second catalyst to produce an aromatic-rich stream, the metal oxide loading of the second catalyst can be from about 0.2 to about 1.5 weight % (wt %), e.g., from about 0.4 to about 0.6 wt %, from about 0.6 to about 0.8 wt %, from about 0.8 to about 1.0 wt %, from about 1.0 to about 1.2 wt %, from about 1.2 to about 1.4 wt % or from about 1.4 to about 1.5 wt %. In certain embodiments, the promoter that is included in the second catalyst for producing an aromatic-rich stream can be in the amount from of 0.025 to about 0.2 wt %.

In certain embodiments, where the method includes catalytic cracking of the hydrogenated stream in the presence of a second catalyst to produce an olefin-rich stream, the metal oxide loading of the second catalyst can be from about 2.0 to about 10 wt %, e.g., from about 2.0 to about 3.0 wt %, from about 3.0 to about 4.0 wt %, from about 4.0 to about 5.0 wt %, from about 5.0 to about 6.0 wt %, from about 6.0 to about 7.0 wt %, from about 7.0 to about 8.0 wt %, from about 8.0 to about 9.0 wt % or from about 9.0 to about 10.0 wt % metal oxide loading. In certain embodiments, for the production of an olefin-rich stream, the second catalyst can be a silica-alumina/ZSM-5 catalyst with or without a metal oxide. In certain embodiments, the second catalyst used for the production of an olefin-rich stream can include Pt and/or Pd loaded onto a zeolite or Ni and/or W loaded on silica and/or alumina. For example, and not by way of limitation, Pt and/or Pd can be loaded onto a zeolite at about 0.3 to about 0.5 wt %. In certain embodiments, Ni and/or W can be loaded onto alumina-silica at a range of about 3 to about 20 wt %. In certain embodiments, a promoter such as, but not limited to, Nd, Ge or Ir, will not be added to the second catalyst for the production of an olefin-rich stream. In certain embodiments, a promoter such as, but not limited to, Ge, will be added to the second catalyst for the production of an olefin-rich stream at a range from about 0.025 to about 0.2 wt %. In certain embodiments, the hydrogenated stream contacts the catalyst from about 0.1 to about 10 seconds to produce an olefin-rich stream.

In certain embodiments, and as shown in FIG. 1, the method 100 can further include hydrodealkylating the aromatic-rich stream in the presence of a third catalyst to produce a benzene-rich stream 103. In certain embodiments, hydrodealkylation can occur in the presence of hydrogen, e.g., at a hydrogen to hydrocarbon ratio of about 3:1. In certain embodiments, hydrodealkylation of the aromatic-rich stream can occur at a temperature from about 590° C. to about 640° C., e.g., from about 600° C. to about 640° C., from about 610° C. to about 640° C., from about 620° C. to about 640° C. or from about 630° C. to about 640° C. In certain embodiments, the hydrodealkylation step can be performed at a pressure from about 40 to 60 bar, e.g., from about 45 bar to about 60 bar, from about 50 bar to about 60 bar, from about 55 bar to about 60 bar. In certain embodiments, the weight hourly space velocity (WHSV) can be from about 2.0 to about 10 per hour.

Alternatively, the aromatic-rich stream can be subjected to toluene disproportionation to obtain a benzene-rich stream (see 103 of FIG. 1). In certain embodiments, the toluene disproportionation process can be performed at a temperature from about 300° C. to about 470° C., e.g., from about 300° C. to about 320° C., from about 300° C. to about 340° C., from about 300° C. to about 360° C., from about 300° C. to about 370° C., from about 300° C. to about 380° C., from about 300° C. to about 400° C., from about 300° C. to about 420° C., from about 300° C. to about 440° C. or from about 300° C. to about 460° C. In certain embodiments, the toluene disproportionation process can be performed at a pressure from about 40 bar to about 45 bar. In certain embodiments, the reactions that take place during toluene disproportionation are shown in Formulas 1 and 2.

Disproportionation: $2C_7H_8 \rightarrow C_6H_6 + C_8H_{10}$ [Formula 1]

Transalkylation: $C_9H_{12} + C_7H_8 \rightarrow 2C_8H_{10}$ [Formula 2]

Alternatively and/or additionally, and as shown in FIG. 1, the method 100 can include subjecting the aromatic-rich stream to mild hydrocracking 105, e.g., to convert any C6 non-aromatics to benzene, in the presence of a third catalyst. In certain embodiments, mild hydrocracking of the aromatic-rich stream produces a benzene-rich stream. In certain embodiments, mild hydrocracking can occur in the presence of hydrogen, e.g., at a hydrogen to hydrocarbon ratio of about 3:1. In certain embodiments, the mild hydrocracking of the aromatic-rich stream can occur at a pressure from about 5 bar to about 20 bar, e.g., from about 5 bar to about 10 bar, from about 10 bar to about 15 bar or from about 15 bar to about 20 bar. In certain embodiments, the mild hydrocracking step can occur at a temperature from about 400 to about 550° C., e.g., from about 400 to about 425° C., from about 425 to about 450° C., from about 450 to about 475° C., from about 475 to about 500° C., from about 500 to about 525° C. or from about 525 to about 550° C. In certain embodiments, the weight hourly space velocity (WHSV) can be from about 2.0 to about 10 per hour.

In certain embodiments, the benzene-rich stream produced by hydrodealkylation, hydrocracking and/or toluene disproportionation process can include greater than about 60%, greater than about 70 wt %, greater than about 80 wt %, greater than about 90 wt % benzene, greater than about 95 wt % benzene, greater than about 99 wt % benzene or greater than about 99.9 wt % benzene. In certain embodiments, the benzene-rich stream can further include greater than about 5%, greater than about 10 wt % or greater than about 15 wt % toluene. In certain embodiments, the benzene-rich stream can include greater than about 0.2 wt %, greater than about 0.5 wt %, greater than about 1.0 wt %, greater than about 1.5 wt %, greater than about 2.0 wt %, greater than about 2.5 wt % or greater than about 3.0 wt % of ethyl benzene. In certain embodiments, the benzene-rich stream can include greater than about 0.2 wt %, greater than about 0.5 wt %, greater than about 1.0 wt %, greater than about 1.5 wt %, greater than about 2.0 wt %, greater than about 2.5 wt % or greater than about 3.0% of ethyl benzene. In certain embodiments, the benzene-rich stream can include greater than about 0.1 wt %, greater than about 0.5 wt %, greater than about 1.0 wt %, greater than about 1.5 wt % or greater than about 2.0 wt % of cumene. In certain embodiments, the benzene-rich stream can include greater than about 1.0 wt %, greater than about 2.0 wt %, greater than about 3.0 wt %, greater than about 4.0 wt % or greater than about 5.0 wt % of biphenyl. In certain embodiments, the benzene-rich stream can further include naphthalene. In certain embodiments, the benzene-rich stream can include from about 70 to about 90 wt % benzene, from about 5 to 15 wt % toluene, from about 0.2 to 3 wt % ethyl benzene, from about 0.1 to 2 wt % cumene, from about 1 to 5 wt % biphenyl and the remaining wt % can be naphthalene. In certain embodiments, where the aromatic-rich steam is subjected to hydrodealkylation and is not subjected to extraction, the benzene-rich stream can include greater than about 99.9 wt % benzene.

In certain embodiments, the third catalyst, which can be used for hydrodealkylation or mild hydrocracking, can include chromia, alumina, and platinum on a zeolite support. Non-limiting examples of zeolites are disclosed above. For example, and not by way of limitation, the third catalyst can include about 15% chromia-alumina and about 1% platinum on Zeolite-Y.

In certain embodiments, and as shown in FIG. 1, the method 100 can further include extracting benzene, toluene and/or xylene (BTX) from the aromatic-rich stream, e.g., in the absence of mild hydrocracking and/or hydrodealkylation, the olefin-rich stream and/or the benzene-rich stream to obtain a high purity benzene product stream 104. In certain embodiments, BTX extraction can be performed using a liquid-liquid extraction process (e.g., the UOP Sulfolane™ process; the Axens Sulfolane process; and/or the Lurgi Arosolvan process) or extractive distillation (e.g., the Axens dimethylformamide process; the Lurgi Distapex process; the Krupp Uhde Morphylane™ process; and/or the GT-BTX process (GTC Technology LLC)). In certain embodiments, the BTX liquid-liquid extraction process can be performed at a temperature from about 200 to about 350° C. and at a pressure from about 2 bar to about 10 bar. In certain embodiments, the extractive distillation process can be performed at a temperature from about 100 to about 250° C. and at a pressure from about 1 bar to about 2 atm. Alternatively and/or additionally, the aromatic-rich stream obtained from the aromatization process can also be subjected to extraction to produce a high purity benzene product stream (see FIG. 1). For example, and not by way of limitation, the high purity benzene product stream can include greater than about 90%, greater than about 91%, greater than about 92%, greater than about 93%, greater than about 94%, greater than about 95%, greater than about 96%, greater than about 97%, greater than about 98% or greater than about 99% benzene. In certain embodiments, extraction of benzene from other aromatics can utilize the differences in the boiling points of the aromatics, e.g., by solvent-based extraction, to yield a high purity benzene product stream. For example, and not by way of limitation, the aromatic-rich stream can be processed within a divided-wall distillation column to simultaneously separate C6 aromatics, e.g., benzene (which has a boiling point of about 81° C.), toluene (which has a boiling point of about 110° C.) and mixed xylene (which has a boiling point of about 134-138° C.) using the differences in their boiling points. In certain embodiments, the benzene fraction obtained from the extraction process can be subsequently treated with a mild hydrocracking process to convert any C6 non-aromatics to benzene to obtain a benzene-rich stream.

The catalysts used in the present disclosure can be prepared by any catalyst synthesis process well known in the art. Examples include, but are not limited to, spray drying, precipitation, impregnation, incipient wetness, ion exchange, fluid bed coating, physical, or chemical vapor deposition.

The following example is merely illustrative of the presently disclosed subject matter and should not be considered as a limitation in any way.

Example

This example discusses the catalyst compositions that can be used for dehydrocycloligomerization (DHCO) reactivity studies.

A C5 feed that contained 50 wt % of olefins and 4% benzene was fed into a lab-scale fixed bed reactor in the presence of a ZSM-S-based catalyst to aromatize the olefins present within the C5 feed. The operating conditions were as follows: 475° C. with a WHSV of 1.4 per hour and a pressure of 600 kPa. These operating conditions led to an aromatics yield of 40-70%. In particular, the aromatics butene, toluene, ethylbenzene, and xylene were generated from the C5 feed using the disclosed aromatization process.

These studies indicate that a catalyst having the following compositions Ga/Nd/ZSM-5, Ga/Pt/Ge/ZSM-5, Pt/Ga/ZSM-5, Pt/Ge/ZSM-5 or Ni—W/Ga/ZSM-5 can aromatize a feed to give a butene, toluene, ethylbenzene, and xylene (BTEX) yield constant for over 150 hours time-on-stream (tos)). The catalysts used in the aromatization process, which are based on a ZSM-5 zeolite, bears a special morphology in the form of small crystallites which reduces coking and makes the catalyst activity stable. The composition of the catalyst along with the process conditions gives the maximum effect in the integrated process. A change in the metal oxide and zeolite proportion would result in either aromatics generation or olefin generation. Metal oxide loading of 0.2-1.5% would generate higher aromatics; whereas, a metal oxide loading in the range of 2-10% would generate olefins. The doping ingredients like Ga, Ge, Nd, Ir, W are in the range of 0.025-0.2 weight (w) %.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

Various patents and patent applications are cited herein, the contents of which are hereby incorporated by reference herein in their entireties.

The invention claimed is:

1. A method for producing aromatics from a coker naphtha stream, the method comprising:
  (a) hydrogenating the coker naphtha stream containing coker naphtha to a certain degree, wherein the coker naphtha has a boiling point of from about 25° C. to 85° C. in the presence of a first catalyst to remove diolefins and sulfur to obtain a hydrogenated stream; and
  (b) subjecting the hydrogenated stream to dehydrocyclo-ligomerization in the presence of a second catalyst to produce an aromatic-rich stream comprising benzene, toluene, and xylene, wherein the coker naphtha stream further comprises from about 0.5 wt % to about 5 wt % aromatics, and wherein the second catalyst has a metal oxide loading of about 0.2 wt % to about 1.5 wt % and is selected from the group consisting of Ga/Pt/Ge/ZSM-5, Pt/Ge/ZSM-5 and Ni—W/Ga/ZSM-5, or the second catalyst is Ga/Nd/ZSM-5.

2. The method of claim 1, wherein the second catalyst comprises from about 0.025-0.2 wt. % of a promoter metal selected from the group consisting of Ga, Ge, Nd and/or W.

3. The method of claim 1, wherein the aromatic-rich stream comprises at least about 40% by weight of aromatic compounds.

4. The method of claim 1, further comprising hydrodealkylating the aromatic-rich stream in the presence of a third catalyst and hydrogen to produce a benzene-rich stream.

5. The method of claim 1, further comprising mild hydrocracking the aromatic-rich stream in the presence of a third catalyst and hydrogen to produce a benzene-rich stream, wherein the mild hydrocracking is conducted at a temperature from about 400 to about 550° C.

6. The method of claim 5, wherein the mild hydrocracking is conducted at a pressure of 5 bar to about 20 bar.

7. The method of claim 6, further comprising mild hydrocracking the benzene-rich stream to produce a stream comprising greater than or equal to about 99% benzene by weight.

8. The method of claim 1, wherein the second catalyst is selected from the group consisting of Ga/Nd/ZSM-5 and Ni—W/Ga/ZSM-5.

9. A method for producing aromatics from a coker naphtha stream containing coker naphtha, the method comprising:
  (a) removing silica and particulates from the coker naphtha stream to obtain a pretreated coker naphtha stream;
  (b) hydrogenating the pretreated coker naphtha stream in the presence of a first catalyst to remove diolefins and sulfur to obtain a hydrogenated stream comprising olefins; and
  (c) subjecting the hydrogenated stream to an aromatization process in the presence of a second catalyst to produce an aromatic-rich stream comprising at least about 40% by weight of aromatic compounds;
  wherein the coker naphtha has a boiling point of from about 25° C. to 85° C. and comprises silica and particulates;
  wherein the second catalyst has a metal oxide loading of about 0.2 wt % to about 1.5 wt % and is selected from the group consisting of Ga/Pt/Ge/ZSM-5, Pt/Ge/ZSM-5 and Ni—W/Ga/ZSM-5, or the second catalyst is Ga/Nd/ZSM-5; and
  wherein the coker naphtha stream comprises from about 0.5 wt % to about 5 wt % aromatics.

10. The method of claim 9, further comprising:
  (d) hydrodealkylating the aromatic-rich stream in the presence of a third catalyst to produce a benzene-rich stream; and
  (e) distilling the benzene-rich stream to obtain a purified product stream comprising greater than or equal to about 99% benzene.

11. A method for producing olefins from a coker naphtha stream containing diolefins and sulfur, the method comprising:
  (a) hydrogenating the coker naphtha stream, wherein the coker naphtha stream contains coker naphtha, wherein the coker naphtha has a boiling point of from about 25° C. to 85° C. in the presence of a first catalyst to remove the diolefins and the sulfur to obtain a hydrogenated stream; and
  (b) subjecting the hydrogenated stream to catalytic cracking in the presence of a second catalyst at a pressure from about 50 to about 300 kPa to produce an olefin-rich stream comprising ethylene, propylene and aromatics, wherein the second catalyst has a metal oxide loading of about 2 wt % to about 10 wt % and is selected from the group consisting of Ga/Pt/Ge/ZSM-5, Pt/Ga/ZSM-5, Pt/Ge/ZSM-5 and Ni—W/Ga/ZSM-5, or the second catalyst is Ga/Nd/ZSM-5;
  wherein the method further comprises removing silica and particulates from the coker naphtha stream prior to hydrogenation; and
  wherein the coker naphtha stream comprises from about 0.5 wt % to about 5 wt % aromatics.

12. The method of claim 11, wherein the second catalyst is selected from the group consisting of Ga/Nd/ZSM-5 and Ni—W/Ga/ZSM-5.

13. The method of claim 11, wherein the olefins-rich stream comprises greater than about 55% of olefins.

14. The method of claim 9, further comprising the steps of:
  (d) hydrodealkylating the aromatic-rich stream in the presence of a third catalyst to produce a benzene-rich stream; and
  (e) distilling the benzene-rich stream to obtain a purified product stream comprising greater than or equal to about 99% benzene.

15. The method of claim 1, further comprising extracting benzene from the aromatic rich stream to obtain a benzene rich stream.

16. The method of claim 1, wherein the coker naphtha stream further comprises from about 20 wt % to about 70 wt % paraffins, from about 20 wt % to about 45 wt % olefins, from about 0.01 wt % to about 3 wt % diolefins and from about 5 wt % to about 15 wt % naphthenes.

\* \* \* \* \*